(12) United States Patent
Rassen et al.

(10) Patent No.: US 9,378,271 B2
(45) Date of Patent: Jun. 28, 2016

(54) DATABASE SYSTEM FOR ANALYSIS OF LONGITUDINAL DATA SETS

(71) Applicant: Aetion, Inc., Forest Hills, NY (US)

(72) Inventors: Jeremy Rassen, New York, NY (US); Allon Rauer, New York, NY (US); Sebastian Schneeweiss, Newton, MA (US)

(73) Assignee: Aetion, Inc., Forest Hills, NY (US)

( * ) Notice: Subject to any disclaimer, the term of this patent is extended or adjusted under 35 U.S.C. 154(b) by 212 days.

(21) Appl. No.: 14/083,406

(22) Filed: Nov. 18, 2013

(65) Prior Publication Data

US 2015/0142821 A1   May 21, 2015

(51) Int. Cl.
 *G06F 17/30* (2006.01)
 *G06F 19/00* (2011.01)

(52) U.S. Cl.
 CPC .... *G06F 17/30619* (2013.01); *G06F 17/30324* (2013.01); *G06F 17/30634* (2013.01); *G06F 19/322* (2013.01); *G06F 19/3443* (2013.01)

(58) Field of Classification Search
 None
 See application file for complete search history.

(56) References Cited

U.S. PATENT DOCUMENTS

| | | | | |
|---|---|---|---|---|
| 8,140,562 | B1* | 3/2012 | Kuraoka | G06F 17/30643 707/767 |
| 8,370,597 | B1* | 2/2013 | Chatterjee et al. | 711/170 |
| 2005/0154710 | A1* | 7/2005 | Ruhlow et al. | 707/3 |
| 2006/0059187 | A1* | 3/2006 | Brown | 707/102 |
| 2006/0161557 | A1* | 7/2006 | Dettinger et al. | 707/100 |
| 2007/0239508 | A1* | 10/2007 | Fazal | G06Q 10/0637 705/7.36 |
| 2008/0010254 | A1* | 1/2008 | Settimi | 707/3 |
| 2008/0091638 | A1* | 4/2008 | Suzuki | 707/1 |
| 2009/0299767 | A1* | 12/2009 | Michon et al. | 705/3 |
| 2010/0114900 | A1* | 5/2010 | Anderson | 707/741 |
| 2013/0173306 | A1* | 7/2013 | Sasidhar | 705/3 |

\* cited by examiner

*Primary Examiner* — Anh Tai Tran
(74) *Attorney, Agent, or Firm* — Lowenstein Sandler LLP; Cicero H. Brabham, Jr.

(57) ABSTRACT

A database system performs analytics on longitudinal data, such as medical histories with events occurring to patients over time. Input data is processed into streams of events. A set of indexes of event characteristics is generated. A set of patient event histories, partitioned by patient, is generated. Several copies of event data are stored, each copy being structured to support a specific analytical task. Data is partitioned and distributed over several hardware nodes to allow parallel queries. Definitions of sets of candidate patients are translated into sets of filters applied to the set of indexes. Data for these candidates are input to analytical modules. Reports from analysis are automatically generated to be compatible with standard guidelines for reporting. Workflows support one task or a set of closely related tasks by offering the user a defined sequence of query options and analytic choices specifically arranged for the task.

14 Claims, 6 Drawing Sheets

PATIENT RECORD 400

PATIENT IDENTIFIER 402

GENDER CODE 404

RACE CODE 406

BIRTHDATE 408

PRIMARY STORAGE FIELD 410

START DATE 412

END DATE 414

LOCATION IDENTIFIER 416

EVENT TYPE 418

RELEVANT VALUES 419

SECONDARY STORAGE FIELDS 420

KEY N 422

VALUE N 424

KEY N+1

VALUE N+1

DATABASE SYSTEM FOR ANALYSIS OF LONGITUDINAL DATA SETS

BACKGROUND

There has been an increasing interest in analyzing large, longitudinal data sets, including data collected from the routine operation of systems with which people interact over time ("real world data"), especially in the field of health care. For example, real world data, in contrast to clinical data from controlled, randomized trials, is analyzed to help evaluate safety, effectiveness and/or value of pharmaceuticals and medical devices. Such real world data can include medical records, insurance claims, prescription data and the like.

There are established principles from the fields of epidemiology and health research regarding performing analytics on longitudinal, real world data. For example, there are well-known statistical methods to apply to data to assess the safety, effectiveness and/or value of medical treatments or interventions ("treatments", which include, but are not limited to, prescription and over-the-counter drugs, medical devices, and procedures). Generally, assessments compare a treatment to no treatment, while comparative assessments compare a treatment to another treatment. In particular, the main challenge in dealing with real world data rather than randomized trial data is that patients generally receive treatments not randomly but rather because they require treatment for a medical condition. Thus, it can be difficult to assess whether a treatment reduces risk of a medical outcome when the patient by definition is already at elevated risk for that outcome. Statistical adjustment techniques can help reduce such confounding effects.

To use these statistical techniques, complex queries are applied to the data to define different groups of patients, and to extract the patients' detailed data, which are then submitted to analytical software to evaluate safety, effectiveness or value. One challenge with applying these statistical methods to real world data is the performance of the computer system in accessing the data.

Beyond statistical and performance issues, investigators wishing to characterize the safety, effectiveness or value of treatments face challenges in assembling data for the inquiry, in maintaining and preserving data to provide for reproducibility of results over time, in providing a clear audit trail of how the inquiry was carried out and with what specific data and methodologies, and in executing inquiries that span multiple databases. Issues of reproducibility and auditability are of particular importance to government regulators and to insurance carriers and others who pay for medical services.

SUMMARY

This Summary introduces selected concepts in simplified form that are further described below in the Detailed Description. This Summary is intended neither to identify key or essential features of the claimed subject matter, nor to limit the scope of the claimed subject matter.

A database system performs analytics on longitudinal data, which represents a time series of events, such as medical histories with a sequence of events occurring to patients over time. Input data is normalized and processed into streams of events. A set of indexes of event characteristics is generated to enable fast discovery of candidate patients. A set of patient event histories, partitioned by patient, is generated for evaluating complex user-specified criteria on a per-patient basis. Several copies of event data are stored, each copy being structured to support a specific analytical task and workflow. Data is partitioned and distributed over several hardware nodes to allow parallel queries. Sets of patient criteria, including demographic characteristics and event exposures, are defined and translated into sets of filters. The structure of the data allows the sets of filters to be applied to the set of indexes in a manner that rapidly generates results, thus allowing candidate sets to be identified. Data for these candidates are input to analytical modules which compute various measures and then perform statistical analyses on those measures. Reports from the analyses are automatically generated to be compatible with standard guidelines for reporting.

A workflow for using such a database system allows a user to define measures based on events in the time series of events stored for patients and carry out an analytic plan. A cohort for analysis is defined based on these measures. Other aspects of an analysis also are defined by reference to the defined measures. After a cohort is identified, additional measures for the cohort are computed, the analysis is performed and a report is generated.

In the following description, reference is made to the accompanying drawings which form a part hereof, and in which are shown, by way of illustration, specific example implementations of this technique. It is understood that other embodiments may be utilized and structural changes may be made without departing from the scope of the disclosure.

DETAILED DESCRIPTION

The following section provides an example operating environment in which longitudinal data is processed and stored in a database, and then analyzed.

Figure 1:
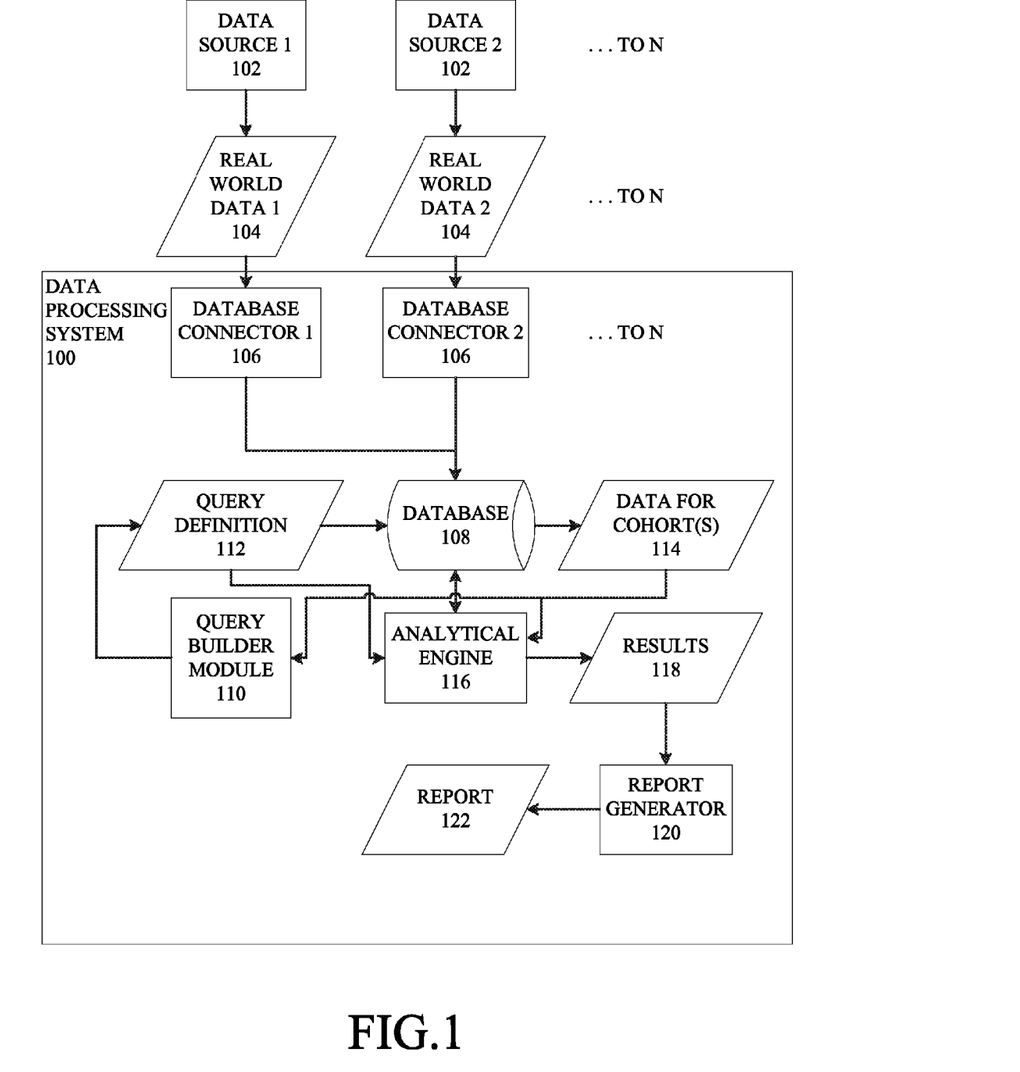
FIG. 1 is a block diagram of an example database system supporting longitudinal data analysis.

Referring to FIG. 1, one or more data sources 102 which provide real world data 104 to a data processing system 100. The data sources generally include a form of storage medium which the data processing system 100 can access to receive the real world data 104. For example, the data source can be a computer, such as described in connection with FIG. 6 below, and accessible over a computer network from which the data 104 can be received, both periodically or upon request. As another example, the data source can be a storage medium accessible by a computer in the data processing system 100 from which the data 104 can be retrieved. The real world data is longitudinal data, which represents a time series of events, such as medical histories with events occurring to patients over time (often years). Such real world data can include, for example, medical records, insurance claims, prescription data and the like. The data processing system 100 receives, processes, stores and analyzes the real world data 104.

The data processing system 100 includes one or more database connectors 106. A database connector is implemented using a computer program on a computer, such as a computer described in connection with FIG. 6 below, and generally is specially-programmed to process real world data 104 from a particular data source 102. Such programming is typically involved because each data source is different, with the real world data 104 being in a different format from data source to data source.

Each database connector 106 processes data 104 from its corresponding data source 102 into a standard format for storing data in a database 108, to be described in more detail below.

Given the data in the database 108, one or more users can access the data to perform various analyses and generate reports using results from those analyses. To assist in those activities, the data processing system 100 includes one or more query builder modules 110. A query builder module 110 is implemented using a computer program on a computer, such as a computer described below in connection with FIG. 6. The query builder module receives input from a user indicating one or more query definitions 112 which define a data set from within the database. The query builder module allows the user to specify whether to draw data from one or several underlying real world data sets that are stored in the database. In the case of medical information, a query definition 112 is processed on the database to identify a set of patients that have certain events, specified in the query definition, occurring in their history. This set of patients is called a cohort. The query builder module has a user interface through which a user enters data defining a query definition 112. The query builder module can interact with the user to build a query definition 112 and then apply the query definition to the database. The database processing is then begun immediately. The database 108 can provide data 114 about the cohort to the query builder module, to allow the query builder module to communicate information to the user, such as through a display (not shown). Thus the user can review data about the cohort and evaluate, accept or revise the query definition, in a real-time, interactive fashion. The query builder module can allow query definitions to be edited and stored for later use. To allow analyses to be reproducible, when a query definition is accepted and stored, a distinct version of that query definition, including the underlying concepts such as its measure definitions, is created. The creation of each version is logged by the data processing system 100, serving as an audit trail for the query design.

After query definitions are accepted, versioned, and stored, the query definitions 112 also are passed to an analytic engine 116 which uses one or more query definitions to perform various analyses on data in the database 108. The kinds of analyses that can be performed by an analytical engine 116 can be computation of measures, examples of which are defined below, from the data 114 for a cohort, and/or any well-known statistical methods applied to the longitudinal data retrieved from the database and/or measures derived from such longitudinal data. Such statistical methods can include those for assessing safety, effectiveness and/or value related to treatments, medical conditions, medicines, medical devices and the like. Such statistical methods can include statistical adjustment techniques that address the problem of confounders in the longitudinal data sets. Such statistical adjustment techniques utilize data obtained for different subsets of a cohort as specified by the query definitions. To allow analyses to be reproducible, the query definition version and cohort data used for the analysis are stored, and can be retrieved in the future to re-execute the analysis and obtain identical results, or to execute a different analysis on the stored cohort to study other aspects of that population. The data processing system 100 logs the execution of the analysis, including the query definition, such that an audit trail is available.

The results 118 of analyses performed by an analytical engine 116 can be provided to a report generator 120 to generate one or more reports 122 using such results. The reports from analyses can be automatically generated to be compatible with standard guidelines for reporting.

As an example report, for most peer-reviewed published articles in the medical field, papers and other reports generally have four sections: an introduction, a presentation of scientific methods, the results of the research (including figures and tables), and a discussion. While the introduction and the discussion are subjective and thus not good candidates for automation, the report generator can automatically document the methods of the analysis and the results. Such documentation can be compatible with internationally-accepted guidelines for complete reporting, such as the STROBE ("STrengthening the Reporting of OBservational studies in Epidemiology") guidelines for reporting on observational (non-randomized) research, and can meet guidance on Periodic Benefit Risk Evaluation Reports and other guidance approaches adopted by the Food and Drug Administration, European Medicines Agency, and other authorities regulating medical products.

In one implementation, the report generator can provide either or both of an interactive web-based reporting and a comprehensive electronic report in a data file, such as one or more data files in a portable document format (PDF). Such reporting can be provided in a full natural language text (e.g., an English language document structured in paragraphs). The reporting is sufficiently complete such that readers of the report would have the information on analytic processes necessary to reproduce the analysis that had been performed.

Specifically, in one implementation such a report can be an electronic document using a markup language to provide hypertext references such as hyperlinks, and can include elements of the following depending on the analytic workflow: a full description of source data, definitions of drug exposure categories and study outcomes, cross-referenced definitions of patient characteristics measured, cross-referenced definitions of longitudinal events measured, cross-referenced definitions of any other measurements performed, cohort entry and exclusion criteria and analytic plan; tabular, graphical, and/or textual description of results, including but not limited to, 2×2 tables, multivariate adjusted tables, diagnostic figures and plots summarizing all results; a table with references to the text indicating how the STROBE, regulatory, or other guidelines were met; references to scientific literature for analytic techniques used; and quick response (QR) codes or similar readable bar codes for accessing the results in the interactive web environment from the published report. The cross-references noted above allow a reader on an electronic device to hyperlink from the mention of the use of a measure to its definition.

Figure 2:
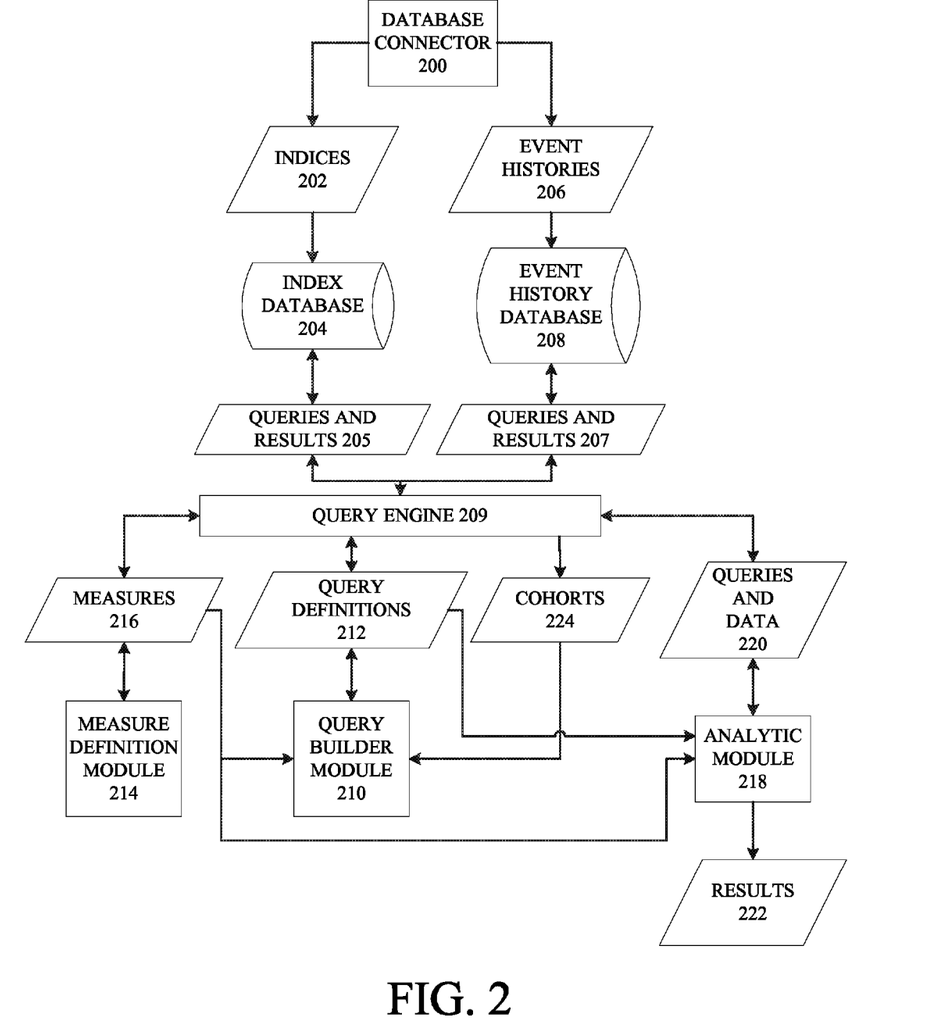
FIG. 2 is a more detailed block diagram illustrating an example implementation of a database system such as described in FIG. 1.

Referring now to FIG. 2, more details of an example implementation of the data processing system 100 will now be described.

In particular, each database connector 200 generates two types of data from the input data, after normalizing the input data and processing it into streams of events. First, a set of indices 202 of event characteristics is generated to enable fast discovery of candidate patients. This set of indices is stored in a first database 204, herein called an index database. Second, a set of patient event histories 206, partitioned by patient, is generated for evaluating complex criteria on a per-patient basis. The event histories are stored in a second database 208, herein called an event history database. Several copies of event data can be stored, each copy being structured to optimally support a specific analytical task. Data can be partitioned and distributed over several computers for storage to allow queries to be performed in parallel. In addition to the patient data, the connector also stores schema metadata about the input data, such as available fields, their data types, and possible values for each field. This information can be used, for example, in the query definition user interface to assist a user in building a query.

The datasets stored in a database 204 or 206 generally are static, i.e., the data is not being dynamically updated while the database is being used for analysis. For example, the data may be updated periodically, e.g., quarterly or every three months, at which time the database is reprocessed and a new structure is generated. Thus, the database can be treated as read-only, which allows some optimization and encoding to be performed before the data is used for analysis to obtain an optimal or near-optimal data format for efficient caching and querying.

In particular, discrete values are encoded as integers, reducing the data to a sequence of integers. These integer arrays are stored in compressed form. This integer-coding scheme assigns the lowest-order integers to those values that occur most in the data, such that these require fewest bits to encode, enabling a more compact representation. Example compression techniques that can be used, depending on the properties of the data, include but are not limited to: Gamma, delta, variable byte, binary interpolative, simple-9, simple-16, PForDelta, OPT-PForDelta, VSEncoding, Varint, Group Varint, Snappy, Rice, and Golomb coding. The input data undergoes a profiling process whereby the system evaluates several such compression techniques, and chooses the one that yields the best compression/performance characteristics. The system records the chosen algorithm, so that the query builder knows how to decode the compressed data.

The data also is divided into two groups: commonly-accessed data and rarely-accessed-data. Determination of the access frequency is done both by gathering of usage statistics and by knowledge of the analytic workflows being performed. This allows for the footprint of commonly-accessed-data to remain smaller than in an otherwise unified storage model. Since user queries access that subset of the data more often, on average a lower volume of data is fed into the processing machinery than if these two classes of data were not segregated.

Figure 4:
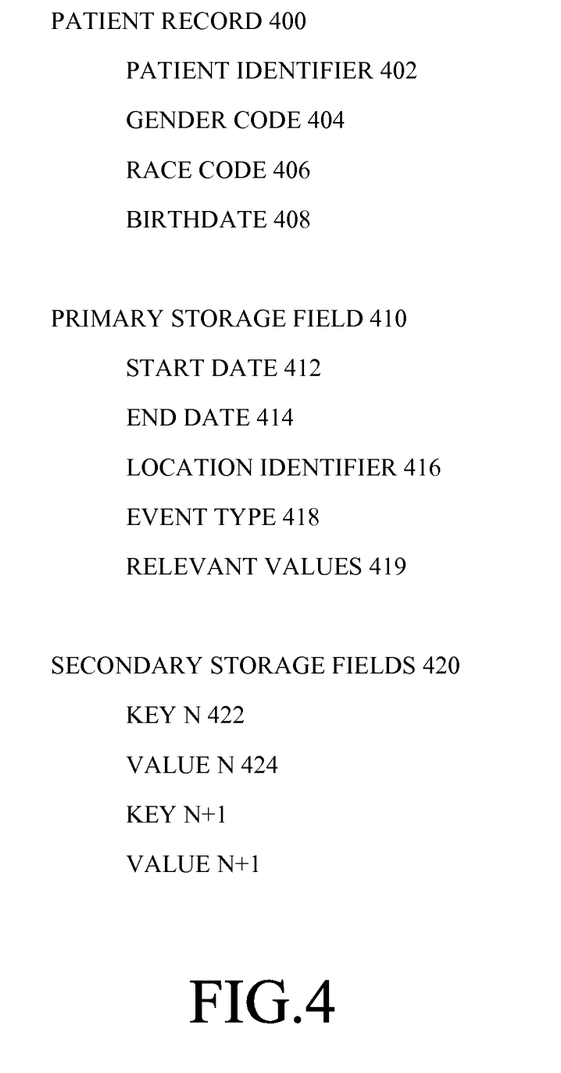
FIG. 4 is a flow chart of an example implementation of a data structure representing longitudinal data.

An example data structure, also illustrated in FIG. 4, is as follows. Each patient record 400 has an identifier 402, a gender code 404, a race code 406 and a birthdate 408. Patient history records are partitioned by patient identifier and an event type (such as a drug or condition), and separated into primary storage and secondary storage. In particular, the primary storage fields 410 include (but are not limited to), a start date 412, an end date 414, a location identifier 416, an event type 418, and any other relevant values 419. The secondary storage fields 420 are generally represented by [key, value] pairs, as indicated at 422 and 424. Metadata can be maintained in the query engine to store the record structure 419 for each event type 418, indicating what those values represent, and indices within the data record of each value type (e.g., drug code is field 4; location is field 3; drug dose code is field 7, etc.)

As an example, e.g. patient 0's longitudinal data can be represented as follows. In this example, strings of text are provided for ease of reading. In practice, the fields are represented by integers to allow the aforementioned integer-array compression techniques to be used, reducing a patient's history to a sequence of integers.

Thus, in one illustrative example of a patient 0 having one drug event and one condition event, the following data can be stored in primary storage:

```
P0/DRUG -> [{1974/01/13, 1974/01/23, PHARMACY, DRUG,
DRUG_CODE_123},
{1974/02/22, 1974/02/23, PHARMACY, DRUG,DRUG_CODE_234}]
P0/COND -> [{1974/01/04, 1974/01/04, INPATIENT, COND,
COND_CODE_4123},
{1974/06/01, 1974/06/24, OUTPATIENT,
COND,COND_CODE_9348}]
```

The following data, in this example, can be stored in secondary storage:

```
P0/DRUG -> [{CLINIC_CODE_789, DOSE_CODE_111,
SOME_OTHER_RARELY_USED_CODE_1983},
{CLINIC_CODE_987,
DOSE_CODE_222,
SOME_OTHER_RARELY_USED_CODE_2019}]
P0/COND -> [{CLINIC_CODE_789, PROVIDER_CODE_ 17897,
SOME_OTHER_RARELY_USED_CODE_36354},
{CLINIC_CODE_987,
PROVIDER_CODE_193847,
SOME_OTHER_RARELY_USED_CODE_4444}]
```

Given data represented in this manner, search engine indexing techniques can be used, in one implementation, to solve the problem of finding patients that have taken a drug or diagnosed with condition. This problem is, in essence, mapped into the problem of finding keywords within documents.

In one implementation, a dictionary of terms (e.g., all drug codes and all condition codes) is defined, and then two indexing approaches are evaluated. The approach that yields the best compression and lookup speed can then be used. These indexes serve to quickly narrow down the entire universe of patients to a manageable set, given high-level criteria (such as whether a patient took a drug, or underwent a procedure). The indexing ignores any longitudinal characteristics, but rather acts as a first-level filter that eliminates subsets of patients whose longitudinal history cannot possibly meet the stated criteria.

In the first approach, an inverted index is created which maps each term to the patient identifiers with the existence of that term in their history. For example, given drugs D1, D2, D3, D4 and four patients with identifiers 0, 1, 2, 3, and the following histories:

```
patient 0 took drug D1
patient 1 took drugs D1, D2, D3
patient 2 took drug D1
patient 3 took drugs D1, D3
``` the following inverted index is generated:

```
D1 --> [0, 1, 2, 3]
D2 --> [1]
D3 --> [1, 3]
D4 --> [ ]
```

Since this index stores only integer identifiers, we can use compression algorithms to effectively pack these integers into fewer bits than their standard representation. Example compression techniques that can be used, depending on the properties of the data, include but are not limited to: Gamma, delta, variable byte, binary interpolative, simple-9, simple-16, PForDelta, OPT-PForDelta, VSEncoding, Varint, Group Varint, Snappy, Rice, and Golomb coding.

In a second approach, a bitmap index is created. In particular, for each term, an N-bit array is created with the Nth bit set if patient identifier N has that term in its history. Various bitmap compression and AND/OR evaluation techniques, such as BBC, EWAH, COMPAX, and CONCISE can be used. Each of these can be evaluated to allow the algorithm that offers the best compression/performance balance for the characteristics of the dataset to be selected.

On top of this indexing strategy, an additional compression and partitioning technique can be used. In particular, the set of patients is segmented into groups of 64 k patients with contiguous patient identifiers. Original patient identifiers are mapped to the offset from the group's start index, such that the range of patient identifiers in each group is [0, 65535] which fits in 16 bits instead of 32, yielding 2:1 compression. For example: group starting offset original patientIds mapped patientIds

| | | | |
|---|---|---|---|
| 0 | 0 | 0...65535 | 0...65535 |
| 1 | 65536 | 65536...131071 | 0...65535 |

Indexes then can be built for each of the groups. This partitioning also provides an added benefit of allowing a parallel search of the indexes, leveraging multiple CPUs and multiple cores available in the computer hosting the database system.

A query engine 209 accesses the databases 204 and 208 using queries that provide results 205. The query engine can be responsive to query definitions 212 from a query builder module 210, providing data 224 about cohorts to the query builder module, or can be responsive to queries 220 which provides data to the analytic module 218. The query definitions 212 built through the query builder module 210 allow the query engine 209 to access the index database 204 to identify patients that can potentially match a query definition 212, thus identifying the cohorts 224. Query definitions can be stored in the query engine 209, for example, or in any other storage readily accessible by the components of the data processing system 100. When stored, various information elements about a query definition can be logged, and versions of the query definition can be maintained, to allow for reproducibility and auditability. The query builder module can retrieve and edit, and store as a new version, previously stored query definitions.

A measure definition module 214 allows a user to define measures 216. Measures are applied to data retrieved for a patient from the event history database 208 and can be used by the query builder module 210 to build query definitions 212. Measures can be stored in the query engine 209, for example, or in any other storage readily accessible by the components of the data processing system 100. When stored, various information about the measure can be logged, including but not limited to version number, keyword, performance metrics, references to the scientific literature, and versions of the measure can be maintained, to allow for reproducibility and auditability. The measure definition module can retrieve and edit, and store as a new version, previously stored measure definitions.

An analytical module receives a query definition 212, cohorts 224 and measures 216 and applies queries 220 to the event history database 208 to receive various data, on which it performs various analyses to provide results 222.

The system can allow for any of a variety of measures to be defined. Such measures can be user defined. A graphical user interface can be provided as part of the measure definition module to allow a user to interactively define measures. Measures also may be defined implicitly by the system. For example, if a user asks the system to limit the patient population to patients over 50 years old, or to statistically adjust an analysis by whether or not a patient is over 50 years old, a measure denoting whether the patient's age is great than 50 years may be implicitly created.

The following describes some example measures. One kind of measure is patient measures. A patient measure is a static property of a patient, generally stored in a "patient demographics" table or similar in the database. These measures can be important for applying statistical adjustment methods. Patient measures include sex, race, socioeconomic status, and the like. Age is a special patient measure that is based on a static property of the patient (his or her birthdate), but is in itself not static. The age patient measure is dynamically calculated based on a day specified by the user in the analytic workflow. For example, in analyses involving drug safety, the age may be calculated as of the date of a patient's first drug exposure.

A patient measure may be used in a filtering or a statistical adjustment context. In a filtering context, the values of the measure are used to limit or otherwise denote certain patients. For example, one may wish to study only patients over 65 years of age, or to exclude those under 18 years of age. In the filtering context, the value of the patient measure is used in such a way as to obtain a dichotomous (true/false value). In a statistical adjustment context, the value of the measure is used in a statistical model, and may require transformation from its raw value to a form more suitable for modeling.

A first sub-type of measure transformation is a dichotomization. Most values can be transformed into dichotomous (binary) states. For example, age can be transformed into a binary value through a measure such as "age is greater than 50".

A second sub-type of measure transformation is a mathematical transformation. Mathematical transformations only apply to numeric values. A mathematical transformation takes the input numeric value (e.g., age) and applies a function to that value. An example measure involves transforming a systolic blood pressure value into the log of the systolic blood pressure. This transformation is done to make the value more normally distributed, and thus more suitable for use in many statistical models. A second example is a transformation of age into the square of age. In this case, a statistical model is able to rapidly raise prediction of a patient's risk as the patient aged.

A third sub-type of measure transformation is a categorization. Categorization can only be applied to numeric values. Categorization involves mapping a range of input values into a single output value. For example, age can be categorized as 10-year bins, with one bin per decade of age. Categorical transformations are used to obtain flexibility in statistical models. To model the risk of heart attack, 5-year age bins may be useful, as risk of heart attack does not increase steadily with age, but rather may be low until age 50, peak at age 75, and decrease thereafter.

Another kind of measure is a longitudinal measure. A longitudinal measure examines the occurrence of events over time. Events are recorded encounters of a patient with the medical system. Events may be point-in-time events (such as the performance of a medical procedure) or events that span multiple days (such as a hospitalization). Events have both natural attributes, such as their date and duration, as well as event-specific attributes, such as procedure codes for procedure events, diagnosis codes for hospitalization events, and drug codes for pharmacy events. Events may also have numeric attributes, such as the cost.

Specifically, a longitudinal measure operates on a stream of longitudinal patient data and returns set of events in the patient history that meet specific criteria. The event data can then be further transformed into characterizations of the patient's longitudinal history (see below). These measures can vary widely in complexity. The following are example sub-types of longitudinal measures.

One sub-type of longitudinal measures is a simple longitudinal measure. A simple longitudinal measure involves a search of the event data with minimal logical criteria applied. An example is "use of statins". This measure could defined as the occurrence of data for pharmacy claim in which the National Drug Code (NDC) attribute is one of the NDC codes for a statin drug.

In a simple longitudinal measure, the logical criteria can reference one or more of the following elements: attributes of the event, such as a pharmacy event's NDC attribute; natural attributes of the event, such as its duration; or numeric attributes of the event, such as its cost.

Simple events may be single criteria (NDC code is a code for a statin drug) or a Boolean OR of multiple criteria (NDC code is a code for a statin drug OR NDC code is code for a diuretic drug).

Another sub-type of longitudinal measures is a complex longitudinal measure. A complex longitudinal measure operates over multiple events simultaneously. It allows all of the logical criteria of a simple longitudinal measure, and further allows specification of time-relative criteria (event with properties x followed by event with properties y, with the second event occurring within z days of the first). For example, "myocardial infarction in hospital" can be defined as any ambulance transport event, followed by either (a) a hospital stay lasting 3 or more days with a primary discharge diagnosis of acute myocardial infarction, or (b) any hospital stay with a primary discharge diagnosis of acute myocardial infarction and with a discharge vital status of deceased.

A longitudinal measure may also be used in a filtering or a statistical adjustment context. In a filtering context, the values of the measure are used to limit or otherwise identify certain patients. For example, one may wish to study only patients who have taken a statin, or to exclude those who have experienced a hospitalization for myocardial infarction. In the filtering context, the filtering occurs based on the existence of the event, or on the existence o the event a certain number of times (e.g., more than two myocardial infarctions). In the statistical adjustment context, the value of the measure may be: whether it occurred at all; the count of times it occurred; or the sum, mean, minimum, or maximum of a numeric attribute associated with all the event occurrences (e.g., sum of cost for myocardial infarction hospitalizations).

When a longitudinal measure is used in a statistical adjustment context, and when the desired value is a count or numeric value, the same three transformations described above (dichotomization, mathematical, categorization) may be applied.

Further, the time pattern of the occurrence of the longitudinal measure may also be used in a filtering or statistical adjustment context. Time characterizations include binning (e.g., occurred 2 times within the month prior to the start of the study, 3 times in the month prior to that, and so forth), numerical characterization of whether an event was occurring more or less frequently prior to exposure (e.g., a score in which negative numbers indicate frequency was decreasing and positive numbers indicate frequency was increasing), and mathematical models such as splines or trajectories.

Another type of measure is a score measure. A score measure builds upon longitudinal measures, but rather than returning events, it returns an accumulated score. Such scores are often used to numerically summarize a patient's risk. For example, Mary Charlson published a "Charlson index" that gives between 1 and 6 points for occurrence of each of a variety of disease conditions (e.g., 1 point for congestive heart failure, 2 points for renal disease, and 6 points for metastatic tumor). The sum of a patient's score is a good marker for severity of disease at a particular point in time. Many such scoring systems exist, and new ones may be conceived by the system's users. Score measures can be implemented as longitudinal measures that have weights for each component condition, with a sum of the weights as the output of the measure.

Figure 3:
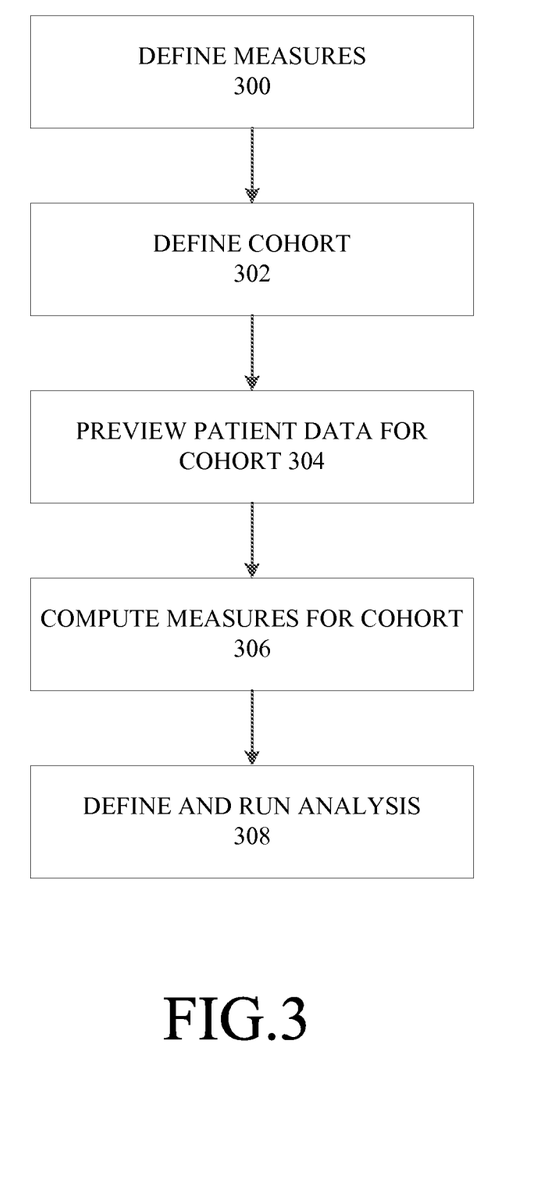
FIG. 3 is a flow chart of an example workflow using a database system such as described in FIG. 2.

An example workflow in using such a system for analyzing longitudinal data will now be described in connection with FIG. 3. The composition of a workflow is defined by the specific task an investigator wants to achieve with use of the analytic engine. Each workflow is designed to support one task or a set of closely related tasks by offering the user a defined sequence of query options and analytic choices specifically arranged for the task; multiple workflows may utilize the same query and analysis components but each workflow has a unique set and sequence of components.

If a researcher is planning to analyze a large set of longitudinal data, the first step is to define 300 various measures to be used in the analysis. As an example, the age and sex of patients of interest can be specified as patient measures. Simple longitudinal measures, such as the use of statins, also can be defined. A graphical user interface can be provided to allow such measures to be selected, added, edited and deleted. A measure can be assigned a name, a description, the patient data from which the measure is derived, and any transformation to be applied to that data, including the type of transformation and a definition of the transformation itself.

After measures are selected, a cohort can be defined 302. A cohort is a subset of the patient population in the database with properties that are interesting for a study. A graphical user interface can be provided through which criteria defining a cohort are specified. Each cohort has a name and description, and source databases from which data is accessed. A cohort may span multiple underlying real world data sources, with matching patients drawn from each of the underlying patient universes. One or more entry criteria, based on defined measures, determine when a patient enters the cohort. One or more exclusion criteria determine when a patient is excluded from the cohort, and can be specified by the user based on defined measures.

Given the defined measures, cohorts and exclusions, a user can preview 304 patient data from the cohort, including but not limited to, sample patient longitudinal event histories, counts of patients in the cohort, and measures applied to patients in the cohort, such as average age, percent male, or percent with prior statin use. These previews may be used to verify the occurrence of outcomes, check for correct specification of cohort inclusion criteria, general quality checking, and for auditability.

After such selection is completed, the user can indicate that a cohort is defined and various measures to be used for analysis are then generated 306 for the cohort. That is, various properties of the longitudinal data for the patients in the cohort can be measured.

A user then can define 308 an analysis to be performed on the cohort and the properties measured for the cohort. An analysis can have a name, description and type, and specify a source cohort. Exposure groups, study outcomes, referent groups, subgroups and confounders are identified by reference to predetermined measures. Details of the analysis to be performed also are defined or selected by the user. The analysis can then be run, to generate results and a report.

Figure 5:
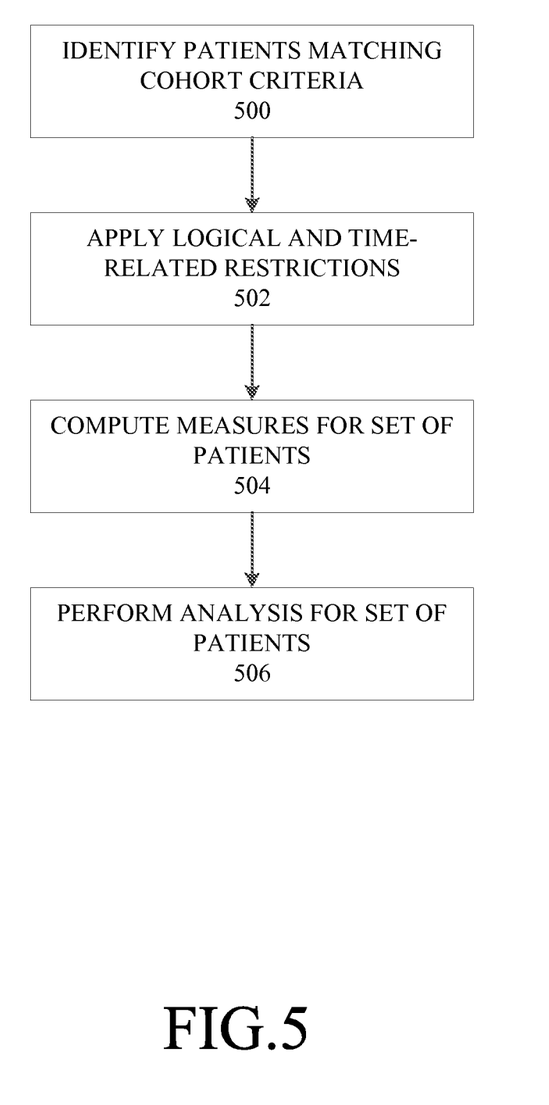
FIG. 5 is a flow chart of an example implementation of applying a workflow of analysis to longitudinal data.

Using such a workflow, and with the data structured in a manner such as described above, the query builder can quickly produce a set of patient identifiers, and associated dates in their historical record, that match a cohort definition. For example, as described in FIG. 5, the query engine first uses the indexes to identify 500 those patients having data that match elements of the cohort criteria, but excluding inter-criterion and other time restrictions. For example, if the cohort is defined as patients that have taken a drug within 30 days of a condition occurring, then the initial set of patients is the set of patients that have taken that drug and that have that condition, and the dates on which those events occurred. The query engine then applies 502 any logical and time-relative elements to the initial set of patients, to arrive at a final set of patients that satisfy all the dependencies. Next, the patient, date tuples are input to the measure calculation engine, which computes 504 various measures for these patients. These measures and the patient data are then provided 506 to the analytical module.

Having now described an example workflow implementation, a general purpose computer in which components of such a system can be implemented will now be described. The following description is intended to provide a brief, general description of a suitable computer with which components of this system can be implemented. The system can be implemented with numerous general purpose or special purpose computing hardware configurations. Examples of well known computers that may be suitable for any given component include, but are not limited to, personal computers, server computers, hand-held or laptop devices (for example, media players, notebook computers, cellular phones, personal data assistants, voice recorders), multiprocessor systems, microprocessor-based systems, set top boxes, game consoles, programmable consumer electronics, network PCs, minicomputers, mainframe computers, distributed computing environments that include any of the above systems or devices, and the like.

Figure 6:
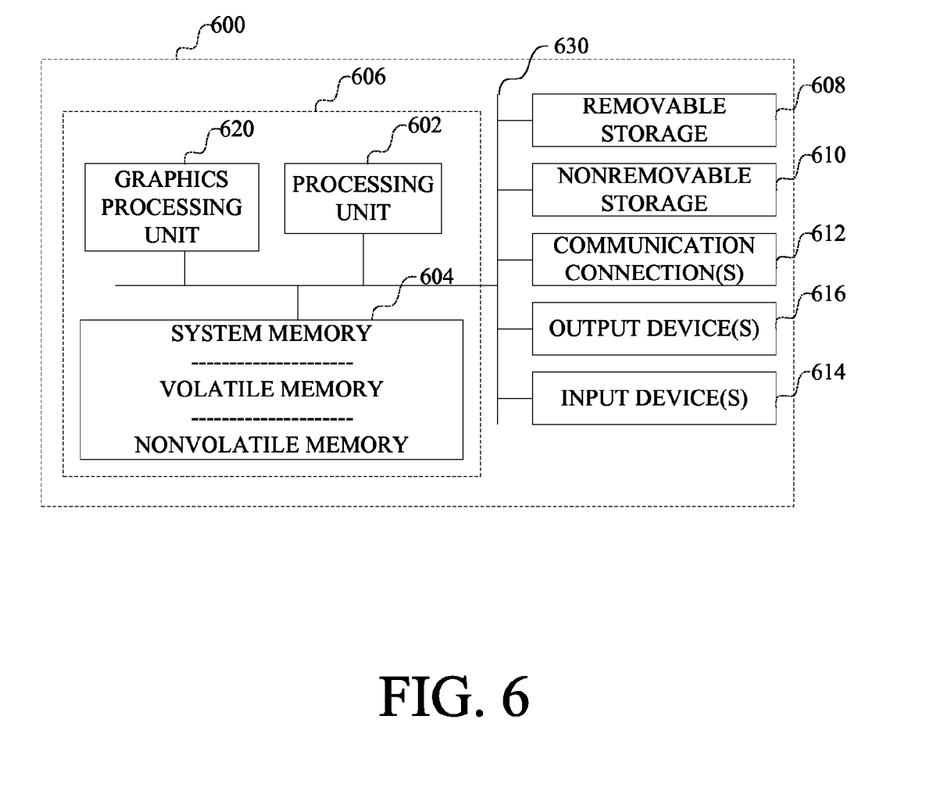
FIG. 6 is a block diagram of an example computer system.

FIG. 6 illustrates an example computer 600. A computer 600 typically includes at least one processing unit 602 and memory 604. The computer may include multiple processing units and/or additional co-processing units such as graphics processing unit 620. Memory 604 may be volatile (such as RAM), non-volatile (such as ROM, flash memory, etc.) or some combination of the two. This configuration is illustrated in FIG. 6 by dashed line 606.

Computer 600 may include additional storage (removable and/or non-removable) including, but not limited to, magnetic or optical disks or tape. Such additional storage is illustrated in FIG. 6 by removable storage 608 and non-removable storage 610. Computer storage media includes volatile and nonvolatile, removable and non-removable media implemented in any method or technology for storage of information such as computer program instructions, data structures, program modules or other data. Memory 604, removable storage 608 and non-removable storage 610 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can accessed by computer 600. Any such computer storage media may be part of computer 600. A storage medium is any addressable medium in which data can be stored in and retrieved from physical storage locations by the computer.

Computer 600 may also contain communications connection(s) 612, which are interface devices that allow a computer to connect to and communicate with other devices over a communication medium. By way of example, and not limitation, communication media includes wired media such as a wired network or direct-wired connection, and wireless media such as acoustic, RF, infrared and other wireless media.

Computer 600 may have various input device(s) 614 such as a keyboard, mouse, pen, camera, touch input device, and so on. Output device(s) 616 such as a display, speakers, a printer, and so on may also be included. All of these devices are well known in the art and need not be discussed at length here.

The various components in FIG. 6 are generally interconnected by an interconnection mechanism, such as one or more buses 630.

Components of such a system may be implemented using specially designed hardware components using software on a general purpose programmable computer, including computer-executable instructions and/or computer-interpreted instructions, such as program modules, being processed by the computer. Generally, program modules include routines, programs, objects, components, data structures, and so on, that, when processed by a processing unit, configure the computer to perform particular tasks or implement particular abstract data types or implement particular components. This system may be practiced in distributed computing environments where tasks are performed by remote processing devices that are linked through a communications network. In a distributed computing environment, program modules may be located in both local and remote computer storage media including memory storage devices.

It should be understood that the subject matter defined in the appended claims is not necessarily limited to the specific implementations described above. The specific implementations described above are disclosed as examples only.

What is claimed is:

1. A database system, comprising:
   a plurality of computing hardware nodes for analyzing longitudinal data for a plurality of entities, each computing hardware node comprises at least a memory to store longitudinal data and a processor coupled to the memory, the longitudinal data comprising events of a plurality of types and dates on which the events occurred with respect to the entities, and an index mapping to map events to the entities; wherein at least one or more of the computing hardware nodes to:
   receive a query definition,
   access the longitudinal data to identify entities having events that match the query definition, each of the identified matching entities comprising a cohort;
   generate a transformation measure with respect to each of the identified matching entities in view of the query definition, wherein to generate the transformation measure, the computing hardware nodes further to:
   identify an event value for the transformation measure associated with at least one entity of the identified matching entities, and
   apply the transformation measure to related events of the longitudinal data associated with the at least one entity to normalize distribution of the event value with respect to the related events;

receive identifiers of the identified matching entities that correspond to the query definition;

access the longitudinal data to retrieve events associated with the identifiers and the generated transformation measures for the identified matching entities; and provide results of a statistical analysis performed on the cohort using the longitudinal data.

2. The database system of claim 1, wherein the at least one or more of the computing hardware nodes further to:

receive the results of the statistical analysis, and provide a report describing the cohort definition, the generated transformation measures and the statistical analysis including references to scientific literature.

3. The database system of claim 1, wherein the index comprises a bitmap index.

4. The database system of claim 1, wherein the index comprises an inverted index.

5. The database system of claim 1, wherein the longitudinal data comprises a first portion stored in a primary storage device and a second portion stored in a secondary storage device, the first portion including data accessed more frequently relative to data accessed in the second portion.

6. The database system of claim 1, wherein the longitudinal data comprises a string of integers, each integer representing a field of data.

7. The database system of claim 1, wherein the computing hardware nodes further to determine a score indicating whether a frequency of occurrence of event data associated with the identified matching entities is increasing or decreasing during a determined time period.

8. The database system of claim 1, further comprising an interactive user interface receiving user input to define transformation measures to apply to the longitudinal data.

9. The database system of claim 1, further comprising an interactive user interface receiving user input to define the query definition to apply to the longitudinal data.

10. The database system of claim 9, wherein the at least one or more of the computing hardware nodes further to log activity related to defining the query definitions.

11. The database system of claim 9, wherein the at least one or more of the computing hardware nodes further to store versions of the query definitions.

12. The database system of claim 1, wherein the at least one or more of the computing hardware nodes further to select a choice of workflows to support one task or a set of closely related tasks by providing a user a defined sequence of query options and analytic selections arranged for the task.

13. A method, comprising:

receiving, by a processing device of a computing hardware node, a query definition associated with longitudinal data, the longitudinal data comprising events of a plurality of types and dates on which the events occurred with respect to a plurality of entities, and an index mapping to map the events to the entities;

accessing the longitudinal data to identify entities having events that match the query definition, each of the identified matching entities comprising a cohort;

generating, by the processing device, a transformation measure with respect to each of the identified matching entities in view of the query definition, wherein the generating comprises:

identifying, by the processing device, an event value for the transformation measure associated with at least one entity of the identified matching entities, and applying, by the processing device, the transformation measure to related events of the longitudinal data associated with the at least one entity to normalize distribution of the event value with respect to the related events;

receiving identifiers of the identified matching entities that correspond to the query definition;

accessing the longitudinal data to retrieve events associated with the identifiers and the generated transformation measures for the identified matching entities; and providing results of a statistical analysis performed on the cohort using the longitudinal data.

14. A non-transitory computer readable storage medium comprising instructions that, when executed by a processing device of a computing hardware node, cause the processing device to:

receiving, by the processing device, a query definition associated with longitudinal data, the longitudinal data comprising events of a plurality of types and dates on which the events occurred with respect to a plurality of entities, and an index mapping to map the events to the entities;

access the longitudinal data to identify entities having events that match the query definition, each of the identified matching entities comprising a cohort;

generate a transformation measure with respect to each of the identified matching entities in view of the query definition, wherein to generate the transformation measure, the processing device further to:

identify an event value for the transformation measure associated with at least one entity of the identified matching entities, and apply the transformation measure to related events of the longitudinal data associated with the at least one entity to normalize distribution of the event value with respect to the related events;

receive identifiers of the identified matching entities that correspond to the query definition;

access the longitudinal data to retrieve events associated with the identifiers and the generated transformation measures for the identified matching entities; and provide results of a statistical analysis performed on the cohort using the longitudinal data.

\* \* \* \* \*